United States Patent
Hansen et al.

(10) Patent No.: US 9,029,594 B2
(45) Date of Patent: May 12, 2015

(54) SEPARATION OF AMMONIUM CHLORIDE FROM THE GAS PHASE OF AN ISOCYANATE PRODUCTION PROCESS

(75) Inventors: Sven Michael Hansen, Leverkusen (DE); Ralf Schneider, Leverkusen (DE); Bernd Schwethelm, Leverkusen (DE); Rolf Schiefer, Leverkusen (DE); Jürgen Dreher, Köln (DE)

(73) Assignee: Bayer MaterialScience AG, Leverkusen (DE)

( * ) Notice: Subject to any disclaimer, the term of this patent is extended or adjusted under 35 U.S.C. 154(b) by 31 days.

(21) Appl. No.: 12/471,528

(22) Filed: May 26, 2009

(65) Prior Publication Data

US 2010/0010257 A1    Jan. 14, 2010

(30) Foreign Application Priority Data

May 31, 2008 (EP) .................... 08009992

(51) Int. Cl.
C07C 263/00 (2006.01)
C07C 263/10 (2006.01)
C07C 263/20 (2006.01)

(52) U.S. Cl.
CPC ............. C07C 263/10 (2013.01); C07C 263/20 (2013.01)

(58) Field of Classification Search
CPC ...................... C07C 263/10; C07C 263/20
See application file for complete search history.

(56) References Cited

U.S. PATENT DOCUMENTS

| 2,680,127 | A | * | 6/1954 | Slocombe et al. ............ 560/347 |
| 3,364,686 | A | * | 1/1968 | Becker ............................ 62/641 |
| 6,800,781 | B2 | | 10/2004 | Herold et al. |
| 2007/0043233 | A1 | | 2/2007 | Sanders et al. |

FOREIGN PATENT DOCUMENTS

DE    270661 A1    8/1989

OTHER PUBLICATIONS

Wikipedia: Deposition and Desublimation definition http://en.wikipedia.org/wiki/Deposition_(physics).*

* cited by examiner

Primary Examiner — Rosalynd Keys
Assistant Examiner — Jennifer C Sawyer
(74) Attorney, Agent, or Firm — Donald R. Palladino; Lyndanne M. Whalen

(57) ABSTRACT

Isocyanates are produced in the gas phase and by-products such as ammonium halides are selectively separated from the gas phase by desublimation.

6 Claims, 1 Drawing Sheet

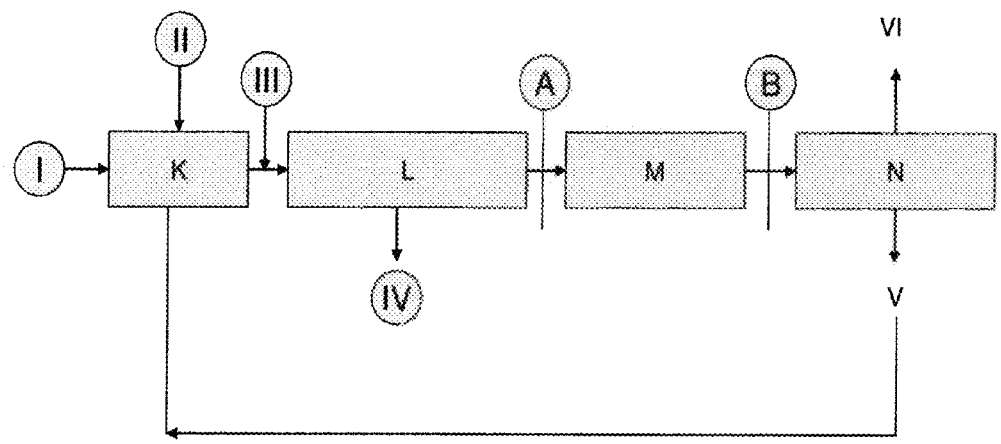

SEPARATION OF AMMONIUM CHLORIDE FROM THE GAS PHASE OF AN ISOCYANATE PRODUCTION PROCESS

BACKGROUND OF THE INVENTION

The present invention relates to a process for the production of isocyanates in the gas phase in which by-products, such as ammonium chloride, are selectively separated from the gas phase by desublimation.

In the preparation of isocyanates by phosgenation of the corresponding amines in the gas phase, impurities in the starting materials or cleavage reactions on heating and overheating of the amines during the transformation into the gas phase result in the formation of ammonia, which can react with hydrogen chloride liberated in the isocyanate formation to form ammonium chloride.

Particularly in the gas treatment sections of the production facility, this leads to solid deposits and pressure drops, so that the plant has to be regularly shut down and cleaned.

This fundamental problem in the preparation of isocyanates by gas-phase phosgenation is disclosed in the prior art but solutions for eliminating it have not yet been proposed.

In principle, however, measures for particle separation from fumes or waste air streams are known. On the basis of the prevailing physical separation principle, customary dust separators are divided into four basic types, with mixed forms of these basic types also being used (e.g., wet electrofilters).

In inertial separators (cyclone, settling chamber and vortex chamber), the mass forces, gravitation force, centrifugal force and inertial force are utilized. They are used as a rule for product recycling or as a preliminary separator. The principle of the wet separator (Venturi scrubber, rotary scrubber, jet scrubber) is based on an accumulation of the dust particles on dispersed liquid drops, the diameter of which is at least an order of magnitude greater than that of the dust particles. Depending on the application, scrubbers may be effective simultaneously as dust separator, quencher, humidifier and/or absorber (e.g., crude gas pretreatment for solvent separation, waste incineration plants). A disadvantage of these separators is the need for frequent aftertreatment of the resulting wastewaters. Electrofilters are the most frequently used plants for processes with a high waste gas temperature and high waste gas volume flow rates such as those which occur in large furnaces, cement furnaces and iron ore sintering furnaces. The dust particles acquire a charge in an electrical field and migrate to the collecting electrode, where they are deposited. Filtering separators utilize the filter effect of woven fabrics, felts, mineral fibers or stainless steel fibers.

A disadvantage, particularly with the separators which operate according to the principle of a gas scrubber, is the comparatively high pressure drop.

SUMMARY OF THE INVENTION

Surprisingly, it has now been found that the principle of resublimation or desublimation can be very successfully used for separating by-products, such as ammonium halides, from gas streams such as those present in the phosgenation of amines in the gas phase, including the related separation and working-up steps, with the result that virtually complete and selective separation from the gas space is achieved.

BRIEF DESCRIPTION OF THE DRAWING

FIG. 1 is a schematic illustration of the customary sequence of a gas-phase phosgenation, points in the process at which such a desublimation according to the invention can be carried out with examples of such possible desublimation points being designated (A) and (B).

DETAILED DESCRIPTION OF THE PRESENT INVENTION

The present invention relates to a process for the production of isocyanates by phosgenation of amines in the gas phase in which by-products are separated from one or more gas streams by desublimation as solid.

In the embodiment of the invention illustrated in FIG. 1, the amine (I) to be phosgenated and the phosgene (II) are fed to the reactor (K). The resulting isocyanate-containing reaction mixture is fed, with addition of a quenching agent (III), e.g. monochlorobenzene, to the isocyanate scrubber (L). After the isocyanate (IV) has been separated off, the gas stream is fed to the condenser (M) and subsequently separated into waste gas (V) and phosgene stream (VI) in the phosgene scrubber (N).

Preferred by-products which are separated from the gas phase in accordance with the present invention are ammonium halides, most preferably ammonium chloride.

In thermodynamics, desublimation is defined as the direct transformation of a substance from the gaseous to the solid state of aggregation. The process itself is designated as resublimation, desublimation, solidification or deposition.

Preferred phosgene still has residual proportions of carbon monoxide and also a content of hydrogen chloride of not more than 15% by weight, preferably from 0.1 to 10% by weight, most preferably from 2 to 8% by weight.

After enrichment with fresh phosgene from the phosgene production, phosgene recycled from the phosgene separation is preferably fed to the amine phosgenation.

Amines which may be used in the process of the present invention include any amino-functional compound having at least one primary amino group, preferably from 1 to 3 primary amino groups, that can be converted into the vapor form. It is unimportant whether the amines are aliphatic, cycloaliphatic, araliphatic or aromatic.

Suitable amino-functional compounds usually have up to 18 carbon atoms. If a plurality of amino groups are present in the molecule, they are generally separated from one another by at least 2 carbon atoms.

Diamines based on aliphatic or cycloaliphatic hydrocarbons having from 2 to 18 carbon atoms are particularly suitable for this purpose.

Examples of suitable diamines include: 1,4-diaminobutane; 1,6-diaminohexane; 1,8-diaminooctane; 1,10-diaminodecane; 1,6-diamino-3,3,5-trimethylhexane; 1-amino-3,3,5-trimethyl-5-aminomethylcyclohexane (IPDA); 2,4- or 2,6-diamino-1-methylcyclohexane; and 4,4'-diaminodicyclohexylmethane. 1,6-Diaminohexane; 1-amino-3,3,5-trimethyl-5-(aminomethyl)cyclohexane; and/or 4,4'-di(aminocyclohexyl)methane are particularly preferred.

Also suitable as starting materials are any of the (cyclo) aliphatic triamines having up to 22 carbon atoms which are stable under the temperature conditions of the process of the present invention and can be converted into the vapor form. Examples of suitable triamines include: triaminocyclohexane; tris(aminomethyl)cyclohexane; and triaminomethylcyclohexane. Also suitable are 1,8-diamino-4-(aminomethyl) octane; 1,6,11-undecanetriamine; 1,7-diamino-4-(3-aminopropyl)heptane; 1,6-diamino-3-(aminomethyl) hexane; and 1,3,5-tris(aminomethyl)cyclohexane.

Aromatic amines which can be converted, preferably without decomposition, into the gas phase can also be used in the process of the present invention. Examples of preferred aromatic amines are toluenediamine (TDA), as 2,4- or 2,6-isomers or as an isomeric mixture thereof; diaminobenzene; 2,6-xylidine; naphthylenediamine (NDA); and 2,4'- or 4,4'-methylene(diphenylamine) (MDA) and isomeric mixtures thereof. 2,4- and/or 2,6-TDA is/are preferred.

Amines of the abovementioned types which can be converted under the chosen process conditions into the gas phase very substantially without decomposition are preferably used. In this context, "very substantially without decomposition" means that not more than 1% by weight, preferably not more than 0.1% by weight, most preferably not more than 0.05% by weight, of the amine used in the vaporization reacts during the heating or overheating with by-product formation, such as ammonia elimination or formation of secondary or tertiary amines.

The amine and phosgene starting materials can be metered in each case into the reaction space together with an inert medium. The inert medium is a medium which is present in gaseous form in the reaction space at the reaction temperature but which does not react with the starting materials or products in the course of the reaction. The inert medium is generally mixed with amine and/or phosgene before the reaction but can also be metered in separately from the starting material streams. Examples of suitable inert media include: nitrogen; noble gases, such as helium or argon; aromatics, such as chlorobenzene, dichlorobenzene or xylene; and carbon dioxide. Nitrogen and/or chlorobenzene is preferably used as the inert medium.

In general, the inert medium is used in an amount such that the ratio of gas volume of the inert medium to gas volume of the amine or phosgene is from 0.001 to 5, preferably form 0.01 to 3, most preferably from 0.1 to 1. The inert medium is preferably introduced into the reaction space together with the amine(s).

The process according to the invention is preferably carried out in a manner such that the amine and phosgene starting materials as well as the isocyanate forming in the reaction zone are in the gaseous state under the reaction conditions, i.e. formation of liquid drops is preferably ruled out.

For providing the above-mentioned reaction conditions, the temperature in the reaction zone is preferably greater than 200° C., more preferably greater than 260° C., most preferably greater than 280° C. The upper limit of the temperature in the reaction zone is preferably below 570° C., most preferably below 500° C.

The reaction of phosgene with amine in the respective reaction zone is conducted at absolute pressures of from more than 0.1 bar to less than 20 bar, preferably from 0.5 bar to 10 bar, more preferably from 0.7 bar to 5 bar, most preferably from 0.8 to 3 bar.

In general, the pressure in the feed pipes into the reaction zone is higher than the pressure in the reaction zone itself. The pressure in the feed lines is preferably from 20 to 2000 mbar, most preferably from 30 to 1000 mbar, higher than the pressure in the reaction zone itself.

In general, the pressure in those regions of the process which are adjacent to the actual reaction zone is lower than the pressure in the reaction zone itself. Preferably, the pressure in such adjacent regions is from 10 to 500 mbar, most preferably from 30 to 150 mbar, lower than in the reaction zone.

In a preferred embodiment of the invention, the starting materials are passed into and through the reaction zone at a flow rate of in each case of from 3 to 100 m/s, preferably of from 10 to 50 m/s.

The flow rates of the two starting materials are preferably adjusted within the above-mentioned ranges so that an average contact time of the reaction mixture containing amine(s) and phosgene of, in general, from 0.01 second to less than 15 seconds, preferably from greater than 0.04 second to less than 10 seconds, most preferably from greater than 0.08 second to less than 5 seconds, is achieved in the reaction zone. "Average contact time" means the time span from the beginning of mixing of the starting materials until the reaction mixture leaves the reaction space and enters into the working-up stage. In a preferred embodiment, the flow in the process according to the invention is characterized by a Bodenstein number of greater than 10, preferably greater than 100 and most preferably greater than 250.

Advantageously, the dimensions of the reaction space and the flow rates are chosen so that turbulent flow, i.e. flow with a Reynolds number of at least 2300, preferably at least 2700, for the reaction mixture is present. The Reynolds number is calculated using the hydraulic diameter of the reaction space.

By means of the turbulent flow, a narrow residence time having a small standard deviation of below 10%, preferably below 6%, is achieved.

The reaction zone preferably has no moving internals.

The reaction zone can be heated via its outer surface. In order to construct production plants having a high plant capacity, a plurality of reactor tubes can be connected in parallel. However, the reaction can also preferably be conducted adiabatically. This means that heating or cooling energy streams do not flow by means of technical measures via the outer surface of the reaction volume. The phosgenation reaction preferably takes place adiabatically.

After the reaction mixture has been reacted in the reaction zone, rapid cooling of the reaction gases after the phosgenation reaction to temperatures below 150° C. is required in order to avoid the formation of undesired by-products due to thermal decomposition of di-/triisocyanate or further reaction by polymerization, since the di-/triisocyanates formed are not thermally stable at the reaction temperatures of from 300 to 570° C. The cooling to temperatures of 100 to 150° C. is conducted in a one-stage or multistage scrubber (quench with wash column) using an inert solvent, as described, for example, in EP-A1 1403248, column 2, line 39—column 3, line 18.

Preferred solvents are hydrocarbons which are optionally substituted with halogen atoms, such as chlorobenzene, dichlorobenzene and toluene. The most preferred solvent is monochlorobenzene. The isocyanate or a solution of the isocyanate prepared, which can also be circulated via a heat exchanger for energy removal, can also be used as the solvent.

During the scrubbing, the isocyanate is selectively transferred to the wash solution. From the remaining isocyanate-free gas (containing excess phosgene, hydrogen chloride, and optionally the inert medium and solvent from the scrubber), the solvent is isolated by partial condensation and then the phosgene may be recovered by, for example, absorption in monochlorobenzene and then fed back to the phosgene starting material stream. After purification in accordance with any of the methods known to those skilled in the art, the hydrogen chloride is further used as a raw material.

The concentrated isocyanate solution obtained in the quench and wash column is preferably freed from physically (dissolved) and chemically bound hydrogen chloride and phosgene by means of rectification and then separated in further distillation phases into pure solvent, low-boiling by-products, pure di- or triisocyanate and high boilers. The isocyanate is preferably used.

The (cyclo)aliphatic isocyanates obtainable by the process of the present invention have hydrolyzable chlorine contents of preferably less than 200 ppm, most preferably less than 80 ppm.

The aromatic isocyanates obtainable by the process of the present invention have hydrolyzable chlorine contents of preferably less than 100 ppm, most preferably less than 30 ppm.

The total chlorine content in the case of the (cyclo)aliphatic and in the case of the aromatic isocyanates is preferably below 800 ppm, most preferably below 500 ppm.

The hydrolyzable chlorine content in isocyanates in the working range w(Cl)>5 mg/kg is determined by urethanization, hydrolysis and potentiometric titration with silver nitrate in a silver/silver chloride combination electrode.

To determine the hydrolyzable chlorine content, the isocyanate sample is mixed with methanol and urethanized for 10 min under reflux. Thereafter, after dilution with water, the mixture is hydrolyzed by boiling under reflux. The ionogenic chlorine formed thereby, after acidification with nitric acid and addition of a known mass of sodium chloride, is titrated argentometrically with a silver nitrate standard solution. The titration is carried out with incremental reagent metering and automatic equivalence point evaluation under drift control (equilibrium titration). The content of hydrolyzable chlorine is calculated from the weight of the isocyanate sample taken and the consumption of silver nitrate standard solution, taking into account the addition.

In the process of present the invention, the desublimation is carried out in the gas path after the reaction zone (K). Suitable locations are after the reaction zone (K) or after inserted apparatuses, such as columns, separators or pumps. Exemplary installation locations are the points characterized by (A) and/or (B) in FIG. 1.

The desublimation is preferably conducted behind the isocyanate scrubber (L) or behind one of the apparatuses thereafter in the gas path.

The desublimation of the by-products, which is essential to the invention, and separation as solid from the gas stream are preferably carried out in an apparatus specially introduced for this purpose into the process. A heat exchanger is preferably used as such an apparatus.

In the heat exchanger, energy transfer takes place between a heat transfer medium and the process stream with the process stream and heat transfer medium being separated from one another and the heat transfer taking place in the separation layer.

Heat exchangers which transport the process stream in tubes and the heat transfer medium around the tubes are suitable. It is possible to introduce internals in the process stream tubes for homogenizing the flow and for better heat transfer into the tubes. Heat exchangers in which such internals are not provided are preferred. So-called plate-type heat exchangers which guide the process stream past hollow plates are particularly preferred, the heat transfer medium being present in the hollow plates.

Preferred plate-type heat exchangers ensure a comparatively long residence time of the process gas stream.

The heat exchanger(s) is/are therefore designed, and the process is operated, so that the specific gas velocity is 2 m/s or less, preferably from 1.5 to 0.05 n/s, most preferably from 1.0 to 0.1 m/s, on passage through the heat exchanger or heat exchangers used for the desublimation.

Preferred plate-type heat exchangers have a surface character which promotes the adhesion of crystallization nuclei, preferably of ammonium halides. This can be achieved, for example, by a rough surface obtained, for example, by blasting processes with substances such as sand or granules.

The plate-type heat exchangers preferably have a minimum of weld seams.

The plate-type heat exchangers are preferably dimensioned so that the deposition of solid is possible over a relatively long period without impairment of the flow behavior of the process gas by the heat exchanger(s) used for the desublimation.

The heat exchangers therefore preferably have a plate register with metal thermal sheet elements having a ratio of width to length in the range from 0.5 to 0.05.

By using plate-type heat exchangers of the above-mentioned type which are dimensioned in the above-described manner, it is possible, without substantially influencing the process gas stream, to remove by-products from the gas stream by desublimation over a period of at least 3000 h, preferably from 3000 to 6600 h, in amounts of at least 60% by weight, preferably at least 80% by weight, most preferably at least 95% by weight, of total by-products.

The plate-type heat exchanger(s) used for the desublimation are preferably incorporated as a bypass into the process and can thus be easily disconnected, cleaned and incorporated again while the process is running.

The cleaning of the plates on the side facing the process stream is conducted with a medium which detaches the adhering by-products to achieve a cleaning effect. The by-products are preferably completely or partly dissolved and removed as solution or slurry from the heat exchanger.

Polar solvents are preferably used for dissolving and washing out the by-products. Polar, protic solvents, such as aqueous, basic solutions, are particularly preferred.

The speed of the cleaning by dissolution and discharge of the by-products is promoted by increasing the flow rate of the solvent during the cleaning process.

Plate-type heat exchangers which have no dead zones or minimized dead zones in the side facing the process gas are particularly preferred. Vertical or horizontal installation is possible.

In addition to the by-products separated off in solid form by desublimation, such as ammonium halides, condensable constituents in liquid form can also be precipitated on the heat exchanger. However, the process according to the invention, including the process parameters of the heat exchangers used for the desublimation, is preferably operated in such a way that deposition of constituents condensable in liquid form from the gas stream does not take place on the heat exchanger or heat exchangers used for the desublimation.

This is preferably achieved by choosing the installation location of the heat exchanger(s) used for the desublimation so that the gas stream is free of liquid constituents or constituents condensable in liquid form. "Free of liquid constituents or constituents condensable in liquid form" means that the gas stream preferably has a proportion of less than 15% by weight, most preferably less than 5% by weight, of constituents which are liquid under the prevailing conditions or are condensable in liquid form.

The desublimation is therefore most preferably carried out only behind the condenser (M).

In the heat exchangers used for the desublimation in accordance with the present invention, heat transfer medium and process gas stream can be fed by the counter-current method or by the co-current method.

The temperature of the heat transfer medium is generally from 150° C. to −60° C., preferably from 100° C. to −40° C., most preferably from 60° C. to −30° C.

The pressure of the process gas in the heat exchanger is in the range of from 1500 mbar (gauge pressure) to 200 mbar abs, preferably from 1000 mbar (gauge pressure) to −500 mbar (gauge pressure), most preferably from 1500 mbar abs to 700 mbar abs.

By operating such a heat exchanger in the manner described above, by-products which can be separated off in solid form are separated from the process gas in a targeted manner and soiling of downstream plant parts, such as pumps, columns, separators, can thus be reduced.

More than 60% by weight of the constituents which can be separated off can thus be separated off by the operation of a heat exchanger. This proportion can be increased to more than 90% by the operation of a plurality of heat exchangers connected in series. The operation of 2, 3, 4 or more heat exchangers connected in series permits the disconnection, cleaning and incorporation of one of the heat exchangers of the connected series without interruption of the reaction. This can also be achieved by a parallel connection of 2, 3, 4 or more heat exchangers, in which switching to the heat exchanger connected in parallel is effected for disconnection, cleaning and reincorporation of a heat exchanger. Series and parallel connection can be combined with one another.

The isocyanates produced in accordance with the present invention are particularly advantageous for used in the preparation of polyurethane coatings, adhesives and sealants. For this purpose, they are preferably first converted into prepolymers, uretdiones, isocyanurates, biurets or allophanates and optionally blocked by methods known to those skilled in the art.

The invention is further illustrated but is not intended to be limited by the following examples in which all parts and percentages are by weight unless otherwise specified.

EXAMPLES

Comparative Example 0.6 mol/s of amine (I) and 1.8 mol/s of phosgene (II) were reacted continuously at an inlet temperature of 300° C. in the gas phase. The reaction gas was precipitated with monochlorobenzene (III) and the reaction vapors were worked up according to the flow diagram shown in FIG. 1. After 25 days, an increase in pressure difference was observed in the phosgene scrubber, which necessitated stopping the reaction after a further 6 days.

Example 1

0.6 mol/s of amine (I) and 1.8 mol/s of phosgene (H) were reacted continuously at an inlet temperature of 300° C. in the gas phase. The reaction gas was precipitated with monochlorobenzene (III) and the reaction vapors were worked up according to the flow diagram shown in FIG. 1. The plate-type heat exchanger, in accordance with the present invention, was introduced in position (A). This plate-type heat exchanger was operated at coolant temperatures of 40° C. and 20° C. at 700 mbar abs. After 31 days, an increasing pressure difference was observable in the phosgene scrubber, which necessitated stopping the reaction after a further 6 days. An analytical evaluation of the deposits in the apparatuses of the waste gas path showed that 5% by weight to 20% by weight of the solid deposits obtained altogether in the process were separated off in the plate-type heat exchanger.

Example 2

0.6 mol/s of amine (I) and 1.8 mol/s of phosgene (II) were reacted continuously at an inlet temperature of 300° C. in the gas phase. The reaction gas was precipitated with monochlorobenzene (III) and the reaction vapors were worked up according to the flow diagram shown in FIG. 1. The plate-type heat exchanger required in the present invention was introduced in position (B). The plate-type heat exchanger was operated at coolant temperatures of from −20° C. at 1200 mbar abs.

Even after 42 days, no increase of the pressure difference in the phosgene scrubber was observable. An analytical evaluation of the deposits in the apparatuses of the waste gas path showed that 60% by weight of the deposits found were separated off in the plate-type heat exchanger.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing an isocyanate comprising:
   (a) feeding an amine and phosgene to a reactor wherein the amine is phosgenated in the gas phase to produce a gas phase isocyanate-containing reaction mixture,
   (b) feeding the gas phase isocyanate-containing reaction mixture and a quenching agent to a scrubber to separate the isocyanate from the gas stream;
   (c) feeding the gas stream from the scrubber to a condenser to produce a gas stream free of liquid constituents or constituents condensable to liquid form;
   (d) feeding the gas stream produced by the condenser to a scrubber that separates the gas stream into a waste gas stream and a phosgene stream; and
   (e) feeding the phosgene produced by the scrubber to the phosgene that is fed to the reactor,
   wherein the process further comprises separating a by-product from a gas stream subsequent to (a) by desublimating the by-product as a solid at a point in the process subsequent to the condenser, and
   wherein the desublimation is carried out in one or more plate-type heat exchangers operated with a heat transfer medium that has a temperature of from 100° C to −40° C.

2. The process of claim 1 in which the amine is triaminocyclohexane; tris(aminomethyl)cyclohexane, triaminomethylcyciohexane; 1,8-diamino-4-(aminomethyhoctane; 1,6,11-undecanetriamine; 1,7-diamino-4-(3-aminopropyl)heptane;1,6-diamino-3-(aminomethyl)hexane; 1,3,5-tris(aminomethyl)cyclohexane; an isomer of toluenediamine (TDA) or a mixture of TDA isomers; diaminobenzene; 2,8-xylidine; naphthylenediamine (NDA); or 2,4'-, 4,4'-methylene(diphenylarnine) (MDA); 1,4-diaminobutane; 1,6-diaminohexane; 1,8-diaminooctane; 1,10-diaminodecane; 1,8-diamino-3,3,5-trimethylhexane; 1-amino-3,3,5-trimethyl-5-aminornethylcyclohexane (IPDA); 2,4- or 2,8-diamino-1-methylcyclohexane; and 4,4'-diaminodicyclohexylmethane 1,6-Diaminohexane; -amino-3,3,5-trimethyl-5-(aminomethy)clcyolohexane; and/or 4,4'-di(aminocyclohexyl)methane.

3. The process of claim 1 in which the amine and phosgene are fed to the reaction zone as a mixture with an inert gas.

4. The process of claim 1 in which the temperature in the reaction zone is greater than 260° C. and below 570° C.

5. The process of claim 1 in which the heat exchanger is designed and the process is operated under conditions such that gas being treated has a velocity of 2 m/s or less on passage through the heat exchanger used for the desublimation.

6. The process of claim 1 in which the by-product separated off is an ammonium halide.

* * * * *